United States Patent [19]

Kishino et al.

[11] Patent Number: 4,985,457
[45] Date of Patent: Jan. 15, 1991

[54] NOVEL CARBOXYLIC ACID ESTERS, METHODS FOR PRODUCING THEM AND INSECTICIDES AND/OR ACARICIDES CONTAINING THEM AS AN ACTIVE INGREDIENT

[75] Inventors: Hiroko Kishino, Kobe; Noritada Matsuo, Itami; Tohei Takagaki, Takarazuka; Kazunori Tsushima, Sapporo; Toshihiko Yano; Yoko Torisu, both of Ashiya, all of Japan

[73] Assignee: Sumitomo Chemical Company, Limited, Osaka, Japan

[21] Appl. No.: 359,395

[22] Filed: May 31, 1989

[30] Foreign Application Priority Data

Jun. 3, 1988 [JP] Japan .................................. 63-138112

[51] Int. Cl.$^5$ ............................................ A01N 53/00
[52] U.S. Cl. ...................................... 514/531; 560/124
[58] Field of Search ............................ 560/124; 514/531

[56] References Cited

U.S. PATENT DOCUMENTS 4,118,505 10/1978 Kitamura ............................ 560/124
4,259,349 3/1981 Bull .................................... 560/124
4,714,712 12/1987 Matsuo .............................. 560/124

FOREIGN PATENT DOCUMENTS 0000229 1/1979 European Pat. Off. .
0202500 11/1986 European Pat. Off. .
291045 11/1988 European Pat. Off. ............ 560/124
2226383 11/1974 France .

Primary Examiner—Michael L. Shippen
Attorney, Agent, or Firm—Stevens, Davis, Miller & Mosher

[57] ABSTRACT

This invention relates to novel carboxylic acid esters represented by the formula (I) below, methods for their production and insecticides and/or acaricides containing them as an active ingredient,

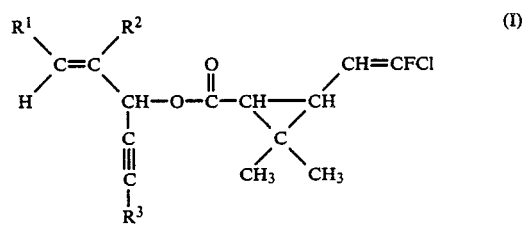

wherein $R^1$ represents a $C_{1-5}$ alkyl group, a $C_{2-4}$ alkenyl group or a $C_{2-4}$ alkynyl group; $R^2$ represents a fluorine atom or a methyl group; and $R^3$ represents a hydrogen atom or a methyl group.

8 Claims, No Drawings

NOVEL CARBOXYLIC ACID ESTERS, METHODS FOR PRODUCING THEM AND INSECTICIDES AND/OR ACARICIDES CONTAINING THEM AS AN ACTIVE INGREDIENT

The present invention relates to a novel carboxylic acid ester, a method for its production and insecticides and/or acaricides containing it as an active ingredient.

Hitherto, the ester compounds, for example, described in JP-B-55-42045, U.S. Pat. No. 4,118,505, European Patent Application No. 229-A and U.S. Pat. No. 4,714,712 are known to have an insecticidal activity.

However, the insecticidal effect of the compounds is not always said to be satisfactory.

In view of the situation like this, the present inventors have extensively studied to develop a compound having excellent insecticidal and/or acaricidal activity, and as a result, have found that an ester compound represented by the formula (I) (hereinafter referred to as present compound) has a very high insecticidal and/or acaricidal activity:

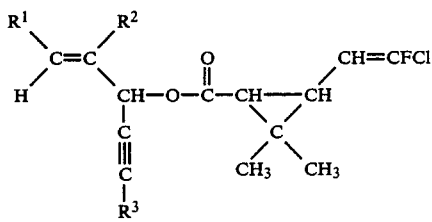

wherein $R^1$ represents a $C_{1-5}$ alkyl group, a $C_{2-4}$ alkenyl group or a $C_{2-4}$ alkynyl group; $R^2$ represents a fluorine atom or a methyl group; and $R^3$ represents a hydrogen atom or a methyl group. The present inventors thus attained to the present invention.

The present compounds have excellent properties such as:

1. Act on various insect and/or acarine pests very rapidly and also with a high insecticidal and/or acaricidal activity.

2. Have a high activity as a volatile formulation or a fumigant.

3. Exhibit an excellent effect on insect and/or acarine pests resistant to organophosphorus or carbamate compounds.

Among the present compounds, preferred ones are those in which $R^3$ is a hydrogen atom. Of these compounds, those in which $R^1$ is a $C_{1-3}$ alkyl group, an allyl group or a propargyl group are more preferred. Typical compounds of the preferred compounds are 1-ethynyl-2-fluoro-2-pentenyl 3-(2-chloro-2-fluorovinyl)-2,2-dimethylcyclopropanecarboxylate and 1-ethynyl-2-methyl-2-pentenyl 3-(2-chloro-2-fluorovinyl)-2,2-dimethylcyclopropanecarboyxlate.

The present compounds can be produced by reacting an alcohol compound represented by the formula (II),

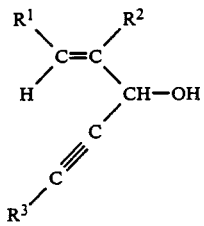

wherein $R^1$, $R^2$ and $R^3$ represent the same meanings as described above, with a carboxylic acid halide represented by the formula (III),

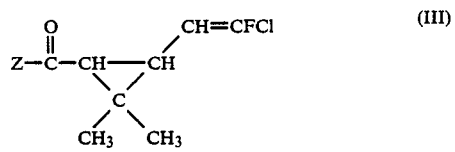

wherein Z represents a halogen atom.

This reaction is usually carried out in an inert solvent (e.g. toluene, benzene, diethyl ether, hexane) at a temperature of from $-30°$ to $100°$ C. for from 30 minutes to 20 hours in the presence of a base (e.g. pyridine, triethylamine). For the carboxylic acid halide represented by the formula (III), a carboxylic acid chloride is usually In the foregoing method, the alcohol compound, a material, represented by the formula (II) can be obtained according to the procedures described in U.S. Pat. Nos. 4,774,369 and 4,263,463. The carboxylic acid halide represented by the formula (III) can be obtained by the known method in European Patent Application No. 229-A.

The present compounds include various optical isomers resulted from an alcohol or acid moiety and geometrical isomers resulted from an acid moiety, and these isomers are also included in the present invention.

For insects and Acarina against which the present compounds are particularly efficacious, there are given the following:

Hemiptera: Planthoppers (Delphacidae) such as smaller brown planthopper (*Laodelphax striatellus*), brown planthopper (*Nilaparvata lugens*) and whitebacked rice planthopper (*Sogatella furcifera*); leafhoppers (Deltocephalidae) such as green rice leafhoppers (*Nephotettix cincticeps, Nephotettix nigropictus* and *Nephotettix virescens*); aphids (Aphididae); bugs; whiteflies (Aleyrodidae); scales; lace bags (Tingidae); and psyllids (Psyllidae); etc.

Lepidoptera: Pyralidae such as rice stem borer (*Chilo suppressalis*), rice leafroller (*Cnaphalocrocis medinalis*) and Indian meal moth (*Plodia interpunctella*); Noctuidae such as tobacco cutworm (*Spodoptera litura*), rice armyworm (*Pseudaletia separata*), cabbage armyworm (*Mamestra brassicae*), turnip cutworm (*Agrotis segetum*), black cutworm (*Agrotis ipsilon*) and Heliothis spp.; Pieridae such as common cabbageworm (*Pieris rapae crucivora*); Tortricidae such as Adoxophyes spp. and Grapholita spp.; Carposinidae; Lyonetiidae; Lymantriidae; Yponomeutidae such as diamondback moth (*Plutella xylostella*); Tineridas such as casemaking clothes moth (*Tinea pellionella*) and webbing clothes moth (*Tineola bisselliella*); etc.

Diptera: Culex spp. such as common mosquito (*Culex pipiens pallens*) and *Culex tritaeniorhynchus;* Aedes spp.

such as *Aedes aegypti*, *Aedes albopictus* and *Aedes togoi;* Anopheles spp. such as *Anopheles sinensis* and *Anopheles stephensi;* Chironomidae; Muscidae such as housefly (*Musca domestica*), little housefly (*Fannia canicularis*) and false stablefly (*Muscina stabulans*); Calliphoridae; Sarcophagidae; Anthomyiidae such as seedcorn maggot (*Delia platura*) and onion maggot (*Delia antiqua*); Tephritidae; Drosophilidae; Psychodidae; black flies (Simuliidae); Tabanidae; and stable flies (Stomoxyidae); etc.

Coleoptera: Scarabaeidae such as cupreous chafer (*Anomala cuprea*) and soybean beetle (*Anomala rufocuprea*); weevils (Curculionidae) such as maize weevil (*Sitophilus zeamais*) and ricewater weevil (*Lissorhoptrus oryzophilus*); Tenebrionidae such as yellow mealworm (*Tenebrio molitor*) and red flour beetle (*Tribolium castaneum*); Chrysomelidae such as western corn rootworm (*Diabrotica virgifera*), southern corn rootworm (*Diabrotica undecimpunctaca howardi*), striped flea beetle (*Phyllotreta striolata*) and cucurbit leaf beetle (*Aulacophora femoralis*); Anobiidae; ladybirds (Coccinellidae) such as twenty-eight-spotted ladybird (*Henosepilachna vigintioctopunctata*); powder post beetles (Lyctidae); false powderpost beetles (Bostrychidae); Cerambycidae; Staphylinidae such as robe beetle (*Paederus fuscipes*); and Dermestidae such as varied carpet beetle (*Anthrenus verbasci*); etc.

Dictyoptera: Blattelidae such as German cockroach (*Blattella germanica*); and Blattidae such as smoky-brown cockroach (*Periplaneta fuliginosa*), American cockroach (*Periplaneta americana*), brown cockroach (*Periplaneta brunnea*) and oriental cockroach (*Blatta orientalis*); etc.;

Thysanoptera: *Thrips palmi* and flower thrips (*Thrips hawaiiensis*); etc.

Hymenoptera: ants (Formicidae); hornests (Vespidae); bethylid wasps (Bethylidae); and sawflies (Tenthredinidae) such as cabbage sawfly (*Athalia rosae ruficornis*); etc.

Orthoptera: mole crickets (Gryllotalpidae); and grasshoppers (Acrididae); etc.

Siphonaptera: Pulicidae such as *Pulex irritans;* etc.

Anoplura: Pediculidae such as *Pediculus humanus capitis* and *Pthirus pubis;* etc.

Isoptera: *Reticulitermes speratus;* and *Coptotermes formosanus;* etc.

Acarina: Tetranychidae such as carmine spider mite (*Tetranychus cinnabarinus*), two-spotted spider mite (*Tetranychus urticae*), Kanzawa spider mite (*Tetranychus kanzawai*), citrus red mite (*Panonychus citri*) and European red mite (*Panonychus ulmi*); Ixodidae such as *Boophilus microplus;* Dermanyssidae; and other mites associated with house dust and stored food such as Acaridae, Pyroglyphidae, and Cheyletidae; etc.

The present compound exhibits a particularly excellent insecticidal and/or acarcidal activity against the foregoing insects and/or acarine pests in the form of a volatile formulation, fumigant, etc.

When the present compounds are used as an active ingredient for insecticidal and/or acaricidal compositions, they may be used as they are without adding any other ingredients. Usually, however, they are formulated into emulsifiable concentrates, wettable powders, flowable concentrates, dusts, granules, oil sprays, aerosols, heating fumigants (e.g. mosquito coils, electric mosquito mats, porous ceramic plates, electric non-mat formulations i.e. heating fumigation of such a form that a part of a porous absorptive wick is dipped in an insecticidal solution to allow it to absorb the solution and said wick is indirectly heated at the top to fumigate the absorbed insecticidal solution), foggings, non-heating volatile formulations, poisonous baits, etc. by mixing with solid carriers, liquid carriers, gaseous carriers, surface active agents, other auxiliaries for formulation, baits, etc. or by impregnating into base material (e.g. mosquito coil carrier, mats).

The present compounds are suitable as an active ingredient particularly for volatile formulations, fumigants, etc.

In these preparations, the content of the present compounds, which are an active ingredient, is from 0.001 to 95% by weight. The solid carriers include for example fine powders or granules of kaolin clay, attapulgite clay, bentonite, terra alba, pyrophyllite, talc, diatomaceous earth, calcite, corn stalk powder, walnut shell powder, urea, ammonium sulfate, synthetic hydrated silicon dioxide, etc. The liquid carriers include for example aliphatic hydrocarbons (e.g. kerosene, hexane, cyclohexane), aromatic hydrocarbon (e.g. benzene, toluene, xylene, methylnaphthalene), halogenated hydrocarbons (e.g. dichloromethane, trichloroethane, carbon tetrachloride), alcohols (e.g. methanol, ethanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil), etc. The gaseous carriers include for example freon gas, butane gas, LPG (liquefied petroleum gas), dimethyl ether, carbon dioxide gas, etc. The surface active agents used for emulsification, dispersion, wetting, etc. include for example anionic surface active agents such as the salt of alkyl sulfates, alkylarylsulfonates, dialkyl sulfosuccinates, the salt or polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation such as fixing agents, dispersing agents, etc. include for example lignosulfonates, alginates, polyvinyl alcohol, gum arabic, molasses, casein, gelatin, CMC (carboxymethyl cellulose), pine oil, agar, etc. The stabilizers include for example alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate), etc.

These preparations are used as they are or diluted with water, etc. Also, they may be used in mixture with other insecticides, acaricides, soil-pest controlling agents, nematocides, fungicides, herbicides, plant growth regulators, synergists, fertilizers, soil improvers, etc.

When the present compounds are used as agricultural insecticides and/or acaricides, their dosage rate is usually from 5 to 500 g/10 ares. When the emulsifiable concentrates, wettable powders, flowable concentrates, etc. are used diluted with water, the application concentration of the active ingredient is from 0.1 to 1000 ppm. The granules, dusts, etc. are used as they are without being diluted.

When the emulsifiable concentrates, wettable powders, flowable concentrates, etc. are used as household and public hygienic insecticides and/or acaricides, they are applied diluted with water to 0.1 to 10000 ppm. The oil sprays, aerosols, fumigants (e.g. mosquito coils, electric mats), volatile formulations, foggings, poisonous baits, etc. are applied as they are.

Although any of these dosage rate and application concentrate depends on the type of preparations, when, where and how these preparations are applied, the kind of pests, the degree of damage, etc., they may be increased or decreased independently of the ranges explained above.

The present invention will be illustrated in more detail with reference to the following production examples, formulation examples and test examples, but it is not limited to these examples.

First, production examples for the present compounds will be shown.

PRODUCTION EXAMPLE 1

Production of the present compound (1)

134 Milligrams of (S)-4-fluoro-3-hydroxy-4-heptene-1-yne and 211 mg of (1R)-trans-2,2-dimethyl-3-(E/Z)-(2-chloro-2-fluorovinyl)cyclopropane-1-carboxylic acid chloride were dissolved in 5 ml of dry toluene, and 108 mg of pyridine was added dropwise thereto with ice-cooling. After completion of the addition, the resulting mixture was stirred at room temperature for 12 hours. The reaction solution was poured into 5 ml of a cooled 5% hydrochloric acid, and the toluene layer was separated. The aqueous layer was extracted twice with diethyl ether. The diethyl ether layers and the toluene layer were combined, washed successively with water and a saturated aqueous sodium chloride solution, and dried over anhydrous magnesium sulfate. The solvent was removed under reduced pressure, and the residue obtained was treated by thin layer chromatography on silica gel (developing solvent, ethyl acetate:hexane=1:7) to obtain 161 mg of the desired compound $[\alpha]_D - 32.17°$.

$^1$H-NMR ppm (solvent, CDCl$_3$; internal standard, TMS): 1.02 (t, 3H), 1.18 (s, 3H), 1.29 (s, 3H), 1.60 (dd, 1H), 1.90–2.45 (m, 3H), 2.55 (d, 1H), 4.32–5.74 (m, 2H), 5.93 (bd, 1H).

$^{19}$F-NMR ppm (solvent, CDCl$_3$; external standard, CF$_3$COOH): −48.43 (dd, 1F), −4.11 (d, ½F), 0.219 (d, ½F).

PRODUCTION EXAMPLE 2

Production of the present compound (2)

Procedure was carried out in the same manner as in Production example 1 except that 130.5 mg of (S)-4-methyl-3-hydroxy-4-heptene-1-yne was used in place of mg of (S)-4-fluoro-3-hydroxy-4-heptene-1-yne, to obtain 169 mg of the desired compound.

$[\alpha]_D - 27.37°$.

$^1$H-NMR ppm (solvent, CDCl$_3$; internal standard, TMS): 0.98 (t, 3H), 1.07 (s, 3H), 1.28 (s, 3H), 1.56 (dd, 1H), 1.75 (s, 3H), 1.90–2.35 (m, 3H), 2.35 (m, 3H), 2.50 (d, 1H), 4.36–5.80 (m, 3H).

$^{19}$F-NMR ppm (solvent, CDCl$_3$; external standard, CF$_3$COOH): −4.33 (d, ½F), −0.025 (d, ½F).

Some of the present compounds obtained in the same manner as above are shown in Table 1.

TABLE 1

$$\begin{array}{c} R^1 \\ \diagdown \\ \phantom{x} \\ H \end{array} C=C \begin{array}{c} R^2 \\ \diagup \\ \diagdown \\ CH-OC-CH-CH \end{array} \overset{O}{\underset{\|}{}} \begin{array}{c} \phantom{x} \\ \diagup \\ C \\ \diagup \diagdown \\ CH_3 \phantom{x} CH_3 \end{array} \begin{array}{c} CH=C \\ \diagup \\ \diagdown \\ Cl \end{array} F$$

| Compound No. | R$^1$ | R$^2$ | R$^3$ | Acid moiety* | Alcohol moiety | Refractive index (°C.) |
|---|---|---|---|---|---|---|
| (1) | C$_2$H$_5$ | F | H | 1R-trans | S | 1.4725 (20) |
| (2) | " | CH$_3$ | " | " | " | 1.4830 (20) |
| (3) | CH$_2$=CHCH$_2$ | F | " | " | RS | 1.4749 (20) |
| (4) | CH≡CCH$_2$ | CH$_3$ | " | 1RS-trans | " | 1.4901 (21) |
| (5) | C$_2$H$_5$ | F | CH$_3$ | 1R-trans | " | 1.4898 (20) |
| (6) | " | " | H | " | " | 1.4721 (20) |
| (7) | n-C$_3$H$_7$ | CH$_3$ | " | " | " | 1.4834 (20) |
| (8) | i-C$_3$H$_7$ | F | " | " | " | 1.4695 (23.5) |
| (9) | C$_2$H$_5$ | " | " | 1RS-cis | " | 1.4733 (22) |
| (10) | " | " | " | 1RS-trans | " | 1.4716 (23.5) |
| (11) | " | CH$_3$ | " | 1R-trans | " | 1.4801 (18.5) |
| (12) | CH$_3$ | " | " | " | S | 1.4857 (22) |

*The E:Z ratio of the —CH=CFCl portion was 1:1.

Production of (1R)-trans-3-(E/Z)-(2-chloro-2-fluorovinyl)-2,2-dimethyl-1-cyclopropanecarboxylic acid, which is a material used in producing the present compounds, will be shown in the following reference example.

REFERENCE EXAMPLE 31.17 Grams of potassium t-butoxide and 72.8 g of triphenyl phosphine were added to 500 ml of dry hexane, and the resulting mixture was cooled to 0° C. under a nitrogen gas stream. A 0° C. solution of 28.6 g of dichlorofluoromethane in 500 ml of dry hexane was added thereto over 20 minutes, and then a hexane solution of 39.4 g of methyl (1R)-trans-2,2-dimethyl-3-formylcyclopropanecarboxylate was added thereto over 25 minutes. The resulting mixture was kept at 55° C. for 1 hour and allowed to stand overnight at room temperature. The insoluble matter was removed by filtration, and the filtrate was distilled under reduced pressure to obtain 30 g of an oily product having a boiling point of 95°–105° C./20 mmHg.

A diethyl ether solution of 30 g of the oily product obtained above by distillation under reduced pressure was added to a solution obtained by adding 140 ml of technical-grade denatured alcohol and water to 200 ml of a saturated aqueous solution of sodium metabisulfite, and the mixture was stirred at room temperature for 30 minutes.

After confirming the disappearance of the aldehyde compound, by gas chromatography, the organic layer was separated, washed with water and dried. The solvent was removed to obtain 11.4 g of methyl (1R)-trans-3-(E/Z)-2-chloro-2-fluorovinyl)-2,2-dimethyl-1-cyclopropanecarboxylate.

$[\alpha]_D + 2.06$ (CHCl$_3$).

$n_D^{23}$ 1.4553.

$^1$H-NMR ppm (solvent, CDCl$_3$; internal standard, TMS) 1.18 (s, 3H), 1.28 (s, 3H), 1.53 (dd, 1H), 1.90–2.40 (m, 1H), 3.68 (s, 3H), 4.32–5.22 (m, 1H):

$^{19}$F-NMR ppm (solvent, CDCl$_3$; external standard, CF$_3$COOH), −4.539 (d, ½F), −0.244 (d, ½F). (−CH=CFCl portion: E/Z=1/1).

5 Grams of the ester obtained above was hydrolyzed with an aqueous methanol solution containing potassium hydroxide of two times by equivalent based on the ester, to obtain 4.2 g of the free acid.

$[\alpha]_D + 6.92$ (CHCl$_3$).

$n_D^{23}$ 1.4728.

$^1$H-NMR ppm (solvent, CDCl$_3$; internal standard, TMS): 1.18 (s, 3H), 1.31 (s, 3H), 1.51 (dd, 1H), 1.93–2.40 (m, 1H), 4.33–5.21 (m, 1H), 10.90 (bs, 1H).

$^{19}$F-NMR ppm (solvent, CDCl$_3$; external standard, CF$_3$COOH): −4.088 (d, ½F), +0.244 (d, ½F).

Formulation examples for insecticidal and/or acaricidal compositions containing the present compounds as an active ingredient will be shown. In the examples, parts are by weight.

FORMULATION EXAMPLE 1

0.1 Part of each of the present compounds (1) to (12), 1 part of xylene and 98.9 parts of kerosene are mixed to obtain an oil spray of each compound.

FORMULATION EXAMPLE 2

Ten parts of each of the present compounds (1) to (12), 14 parts of polyoxyethylene styrylphenyl ether, 6 parts of calcium dodecylbenzenesulfonate and 70 parts of xylene are well mixed to obtain an emulsifiable concentrate of each compound.

FORMULATION EXAMPLE 3

Twenty parts of each of the present compounds (1), (2), (6) and (11), 10 parts of Fenitrothion, 3 parts of calcium lignosulfonate, 2 parts of sodium lauryl sulfate and 65 parts of synthetic hydrated silicon dioxide are well pulverized and mixed to obtain a wettable powder of each compound.

FORMULATION EXAMPLE 4

One part of each of the present compounds (3), (4), (7) and (10), 2 parts of Carbaryl, 87 parts of kaolin clay and 10 parts of talc are well pulverized and mixed to obtain a dust of each compound.

FORMULATION EXAMPLE 5

Five parts of each of the present compounds (5), (8), (9) and (12), 1 part of synthetic hydrated silicon dioxide, 2 parts of calcium lignosulfonate, 30 parts of bentonite and 62 parts of kaolin clay are well pulverized and mixed. The resulting mixture is well kneaded with water, granulated and dried to obtain a granule of each compound.

FORMULATION EXAMPLE 6

0.05 Part of each of the present compounds (1), (2), (6) and (11), 0.2 part of Tetramethrin, 0.05 part of Resmethrin, 7 parts of xylene and 32.7 parts of deodorized kerosene are mixed into a solution. The solution is filled in an aerosol container. After mounting a valve portion on the container, 60 parts of a propellant (liquefied petroleum gas) is charged into the container under pressure through the valve portion to obtain an oil-based aerosol of each compound.

FORMULATION EXAMPLE 7

0.6 Gram of each of the present compounds (1) to (12) is dissolved in 20 ml of methanol, and the resulting solution is uniformly mixed with 99.4 g of a mosquito coil carrier (a mixture of Tabu powder, *Pyrethrum marc* and wood powder in a ratio of 3:5:1) with stirring. After vaporizing methanol, 150 ml of water is added to the residue, and the mixture is well kneaded, shaped into a mosquito coil and dried. Thus, a mosquito coil of each compound is obtained.

FORMULATION EXAMPLE 8

100 Milligrams of each of the present compounds (1) to (12) is dissolved in a proper amount of acetone, and a porous ceramic plate of 4.0 cm×4.0 cm×1.2 cm (thick) is impregnated with this solution to obtain a heating fumigant of each compound.

FORMULATION EXAMPLE 9

500 Milligrams of each of the present compounds (1) to (12) is dissolved in a proper amount of acetone and uniformly coated onto a filter paper of 10 cm×15 cm×0.28 mm (thick). Acetone is removed by air-drying to obtain a room-temperature volatile formulation of each compound.

Test examples on an insecticidal and acaricidal method using the present compounds will be shown below.

The present compounds are shown by Compound Nos. in Table 1, and compounds used as a control are shown by Compound symbols in Table 2.

TABLE 2

| Compound symbol | Structural formula | Remarks |
|---|---|---|
| (A) | CH$_3$O\\ ⧹⧹S<br>    P—S—CHCOOC$_2$H$_5$<br>    ∕         \|<br>CH$_3$O      CH$_2$COOC$_2$H$_5$ | Malathion |

TABLE 2-continued

| Compound symbol | Structural formula | Remarks |
|---|---|---|
| (B) | | Compound No. 4 disclosed in U.S. Pat. No. 4,118,505. |
| (C) | | Compound No. 127 disclosed in U.S. Pat. No. 4,118,505. |
| (D) | | Compound No. 147 disclosed in U.S. Pat. No. 4,118,505. |
| (E) | | Compound No. 74 disclosed in JP-B-55-42045. |
| (F) | (1R-cis) | Compound No. 6 disclosed in EP-229-A. |
| (G) | | Compound No. 9 disclosed in U.S. Pat No. 4,714,712. |
| (H) | | Compound No. 1 disclosed in U.S. Pat. No. 4,714,712. |

TEST EXAMPLE 1

The emulsifiable concentrates of the following present compounds obtained according to Formulation example 2 were each diluted with water to 3.5 ppm. 100 Milliliters of the dilute solution was put in a 180-ml polyethylene cup, and 20 last instar larvae of common mosquito (*Culex pipiens pallens*) were liberated in the cup. Next day, the dead and alive of the larvae were examined to obtain a mortality. This test was repeated twice. The results are shown in Table 3.

TABLE 3

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |

TABLE 3-continued

| Test compound | Mortality (%) |
| --- | --- |
| (12) | 100 |
| No treatment | 2.5 |

TEST EXAMPLE 2

The emulsifiable concentrates of the following present compounds and control obtained according to Formulation example 2 were each diluted 200 times with water (corresponding to 500 ppm), and rice seedings (length, about 12 cm) were dipped for 1 minute in the aqueous dilute solution. After air-drying, the rice seedlings were put in a test tube, and 10 adults of resistant-strain green rice leafhopper (*Nephotettix cincticeps*) were liberated in the test tube. After one day, the dead and alive of the adults were examined to obtain a mortality. This test was repeated twice.

The results are shown in Table 4.

TABLE 4

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (A) | 50 |
| No treatment | 5 |

TEST EXAMPLE 3

Each of the following present compounds controls was diluted with acetone and uniformly coat to the bottom of a glass Petri dish (inside diameter, 9 cm; height, 2 cm; and bottom area, 63.6 cm$^2$) so that the amount of the pesticide was 5 mg/m$^2$. Acetone was removed by air-drying. Thereafter, the top of a polyethylene cup (diameter, 9 cm; and height, 4.5 cm) in which 20 female adults of susceptible housefly of CSMA strain (*Musca domestica*) were liberated, was covered with this Petri dish with nylon net (16 mesh) therebetween so that the insects were not brought into direct contact with the treated surface of the Petri dish. After 120 minutes elapsed, the Petri dish was removed, and water and baits were given The dead and alive after 24 hours were examined to obtain a mortality. This test was repeated twice.

The results are shown in Table 5.

TABLE 5

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100. |
| (10) | 100 |

TABLE 5-continued

| Test compound | Mortality (%) |
| --- | --- |
| (11) | 100 |
| (12) | 100 |
| (B) | 50 |
| (C) | 5 |
| (D) | 2.5 |
| (E) | 0 |
| (F) | 0 |
| No treatment | 2.5 |

TEST EXAMPLE 4

A mosquito coil containing 0.6% of each of the present compounds and controls was prepared according to Formulation example 7.

Ten female adults of common mosquito (*Culex pipiens pallens*) were liberated in a (70 cm$^3$) glass chamber (corresponding to 0.34 m$^3$).

One gram of the mosquito coil was ignited at the both ends and put in the glass chamber. After 10 minutes, the number of the knocked-down insects was examined to obtain a percent knock-down. This test was repeated twice.

The results are shown in Table 6.

TABLE 6

| Test compound | % Knock-down |
| --- | --- |
| (1) | 100 |
| (2) | 100 |
| (6) | 100 |
| (10) | 100 |
| (11) | 100 |
| (B) | 55 |
| (C) | 60 |
| (D) | 55 |
| (E) | 15 |
| (F) | 10 |
| No treatment | 0 |

TEXT EXAMPLE 5

Each of the following present compounds are diluted with acetone to a prescribed concentration and uniformly coated onto a filter paper of 6 cm × 12 cm in size (amount of the pesticide, 200 mg/m$^2$). The paper was folded into two at the center and pasted both sides to prepare a bag. Twenty common grain mites (*Tyrophagus putrescentiae*) were liberated in the bag together with foods, and the top of the bag was closed with a clip. Thereafter, the bag was placed under conditions wherein the temperature was 25° C. and the humidity was 75% R.H. After one day, the dead and alive of the mites were examined to obtain a mortality. This test was repeated twice.

The results are shown in Table 7.

TABLE 7

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |

TABLE 7-continued

| Test compound | Mortality (%) |
| --- | --- |
| No treatment | 7.5 |

TEST EXAMPLE 6

Each of the following present compounds and controls was diluted with acetone and uniformly coated to the bottom of an aluminum dish (inside diameter, 10.5 cm; height, 3 cm; and bottom area, 86.6 cm$^2$) so that the amount of the pesticide was 1000 mg/m$^2$. After removing acetone by air-drying, the treated dish was placed at the center of the bottom of a 0.34 m$^3$ glass chamber [(70 cm$^3$)] (amount of the pesticide in the chamber, 17.7 mg/m$^3$).

After 30 minutes elapsed, the upper surface of the dish was covered with a nylon net (16 mesh) so that the insects were not brought into direct contact with the treated surface of the dish, and ten adults (male:-female=1:1) of susceptible housefly of CSMA strain (*Musca domestica*) were liberated in the glass chamber. Sixty minutes after liberation, the number of knocked-down insects was examined to obtain a percent knock-down. This test was repeated twice.

The results are shown in Table 8.

TABLE 8

| Test compound | % Knock-down |
| --- | --- |
| (3) | 95 |
| (6) | 100 |
| (G) | 0 |
| (H) | 0 |
| No treatment | 0 |

What is claimed is:

1. A compound represented by the formula,

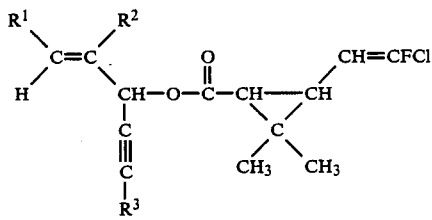

wherein R$^1$ represents a C$_{1-5}$ alkyl group, a C$_{2-4}$ alkenyl group or a C$_{2-4}$ alkynyl group; R$^2$ represents a fluorine atom or a methyl group; and R$^3$ represents a hydrogen atom.

2. A compound according to claim 1, wherein R$^1$ represents a C$_{1-3}$ alkyl group, an allyl group or a propargyl group and R$^3$ represents a hydrogen atom.

3. A compound represented by the formula,

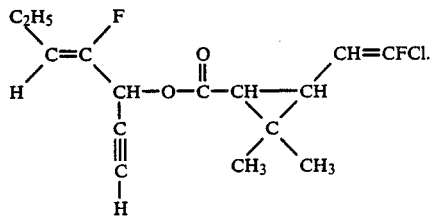

4. A compound represented by the formula,

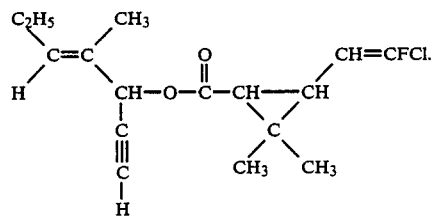

5. An insecticidal and/or acaricidal composition which comprises as an active ingredient an insecticidally and/or acaricidally effective amount of a compound represented by the formula,

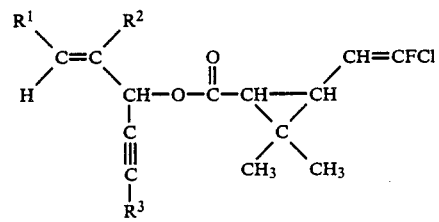

wherein R$^1$ represents a C$_{1-5}$ alkyl group, a C$_{2-4}$ alkenyl group or a C$_{2-4}$ alkynyl group; R$^2$ represents a fluorine atom or a methyl group; and R$^3$ represents a hydrogen atom, and an inert carrier.

6. An insecticidal and/or acaricidal composition according to claim 5, wherein R$^1$ represents a C$_{1-3}$ alkyl group, an allyl group or a propargyl group and R$^3$ represents a hydrogen atom.

7. An insecticidal and/or acaricidal composition according to claim 5, wherein R$^1$ represents an ethyl group and R$^3$ represents a hydrogen atom.

8. A method for controlling insects and/or Acarina which comprises applying an insecticidally and/or acaricidally effective amount of a compound according to claim 1 to the insects and/or Acarina.

* * * * *